United States Patent
Roberts et al.

(10) Patent No.: US 6,974,434 B2
(45) Date of Patent: Dec. 13, 2005

(54) METHODS AND DEVICES FOR MAINTAINING CARDIOPULMONARY BYPASS AND ARRESTING A PATIENT'S HEART

(75) Inventors: Craig P. Roberts, Laguna Niguel, CA (US); John M. Toomasian, Menlo Park, CA (US); Sylvia W. Fan, San Francisco, CA (US)

(73) Assignee: Heartport, Inc., Redwood City, CA (US)

( * ) Notice: Subject to any disclaimer, the term of this patent is extended or adjusted under 35 U.S.C. 154(b) by 89 days.

(21) Appl. No.: 10/193,627

(22) Filed: Jul. 11, 2002

(65) Prior Publication Data

US 2002/0176797 A1 Nov. 28, 2002

Related U.S. Application Data

(62) Division of application No. 09/401,734, filed on Sep. 23, 1999, now Pat. No. 6,443,922, which is a division of application No. 08/789,223, filed on Jan. 24, 1997, now Pat. No. 5,957,879.

(51) Int. Cl.[7] .......................... A61M 37/00; A61M 1/14
(52) U.S. Cl. ...................... 604/6.14; 604/4.01; 604/6.1; 604/6.16; 422/45; 128/DIG. 3
(58) Field of Search ................................ 604/4.01, 5.01, 604/6.06, 6.09, 6.1, 6.11, 6.12, 6.14, 6.16, 6.07, 500, 506–509, 523, 532, 533, 537–38, 264, 27, 28, 30–34, 35, 65–67, 73, 96.01, 99.04, 131, 140, 149, 151; 128/DIG. 3; 606/191–92, 194, 198; 435/283.1, 284.1, 286.5–286.6; 422/44–45

(56) References Cited

U.S. PATENT DOCUMENTS

| 1,756,670 A | 4/1930 | Treat |
| 2,406,207 A | 8/1946 | Desmet |
| 3,254,650 A | 6/1966 | Collito |
| 3,254,651 A | 6/1966 | Collito |
| 3,426,743 A | 2/1969 | Chestnute et al. |

(Continued)

FOREIGN PATENT DOCUMENTS

| WO | WO 97/39784 | 10/1997 |
| WO | WO 97/40754 | 11/1997 |

OTHER PUBLICATIONS

Androsov, "New Method of Surgical Treatment of Blood Vessel Lesions" (1956) Arch. Surg. 73:902–910.

Berggren et al., "Clinical Experience with UNILINK 3M Precise Microvascular Anastomotic Device" Scand J Plast Reconstru Hand Surg. 1993127:35–39.

Cooper et al., "Development of the Surgical Stapler with Emphasis on Vascular Anastomosis," NY Acad. Sci, 1963;25–365–377.

Gentili et al., "A technique for Rapid Non–suture Vascular Anastomosis," Can. J Neuro Sci., 10987;14(1):92–95.

Goetz et al., "Internal Mammary–coronary Artery Anastomosis: A Nonsuture Method Employing Tantalum Rings," J Thorac Card Surg. 1961;41(3):378–386.

(Continued)

Primary Examiner—Patricia Bianco
(74) Attorney, Agent, or Firm—Brian Tomko

(57) ABSTRACT

An endovascular system for arresting a patient's heart and maintaining the patient on cardiopulmonary bypass. A venous cannula, venting catheter and an aortic occlusion device are all coupled together so that the blood drawn into each of these catheters may be fed to a pump. A manifold has valves which control flows through the venous cannula, venting catheter and aortic occlusion device. A blood storage element is also provided so that the amount of blood in the perfusion circuit may be varied if necessary. The blood storage element is preferably positioned in parallel with the pump so that the pump may be used to add and remove blood to and from the blood storage element.

5 Claims, 4 Drawing Sheets

U.S. PATENT DOCUMENTS

| | | | |
|---|---|---|---|
| 3,519,187 A | 7/1970 | Kapitanov | |
| 3,570,497 A | 3/1971 | Lemole | |
| 3,774,615 A | 11/1973 | Lim et al. | |
| 3,792,978 A | 2/1974 | Freedman | |
| 3,881,483 A | 5/1975 | Sausse | |
| 3,949,734 A | 4/1976 | Edwards et al. | |
| 4,192,315 A | 3/1980 | Hilzinger et al. | |
| 4,350,160 A | 9/1982 | Kolesov et al. | |
| 4,352,358 A | 10/1982 | Angelchik | |
| 4,353,368 A | 10/1982 | Slovak et al. | |
| 4,366,819 A | 1/1983 | Kaster | |
| 4,368,736 A | 1/1983 | Kaster | |
| 4,505,414 A | 3/1985 | Filipi | |
| 4,523,592 A | 6/1985 | Daniel | |
| 4,540,399 A | 9/1985 | Litzie et al. | |
| 4,553,542 A | 11/1985 | Schenck et al. | |
| 4,593,693 A | 6/1986 | Schenck | |
| 4,607,637 A | 8/1986 | Berggren et al. | |
| 4,610,656 A | 9/1986 | Mortensen | |
| 4,624,255 A | 11/1986 | Schenck et al. | |
| 4,624,257 A | 11/1986 | Berggren et al. | |
| 4,639,252 A | 1/1987 | Kelly et al. | |
| 4,657,019 A | 4/1987 | Walsh et al. | |
| 4,662,355 A | 5/1987 | Pieronne et al. | |
| 4,665,908 A | 5/1987 | Calkin | |
| 4,666,425 A | 5/1987 | Fleming | |
| 4,671,279 A | 6/1987 | Hill | |
| 4,705,508 A | 11/1987 | Karnavas et al. | |
| 4,747,407 A | 5/1988 | Liu et al. | |
| 4,804,365 A | 2/1989 | Litzie et al. | |
| 4,809,695 A | 3/1989 | Gwathmey et al. | |
| 4,850,954 A | 7/1989 | Charvin | |
| 4,907,591 A | 3/1990 | Vasconcellos et al. | |
| 4,917,087 A | 4/1990 | Walsh et al. | |
| 4,917,090 A | 4/1990 | Berggren et al. | |
| 4,917,091 A | 4/1990 | Berggren et al. | |
| 5,069,661 A | 12/1991 | Trudell | |
| 5,119,983 A | 6/1992 | Green et al. | |
| 5,324,447 A | 6/1994 | Lam et al. | |
| 5,330,503 A | 7/1994 | Yoon | |
| 5,336,233 A | 8/1994 | Chen | |
| 5,342,181 A | 8/1994 | Schock et al. | |
| 5,366,462 A | 11/1994 | Kaster et al. | |
| 5,423,769 A | 6/1995 | Jonkman et al. | |
| 5,425,708 A | 6/1995 | Nasu | |
| 5,478,354 A | 12/1995 | Tovey et al. | |
| 5,522,834 A | 6/1996 | Fonger et al. | |
| 5,540,653 A | 7/1996 | Schock et al. | |
| 5,549,619 A | 8/1996 | Peters et al. | |
| 5,554,162 A | 9/1996 | DeLange | |
| 5,597,378 A | 1/1997 | Jervis | |
| 5,620,452 A | 4/1997 | Yoon | |
| 5,695,504 A | 12/1997 | Gifford, III et al. | |
| 5,702,412 A | 12/1997 | Popov et al. | |
| 5,810,851 A | 9/1998 | Yoon | |
| 5,972,024 A | 10/1999 | Northrup, III et al. | |
| 6,046,046 A * | 4/2000 | Hassanein | 435/284.1 |
| 6,090,096 A * | 7/2000 | St. Goar et al. | 604/509 |
| 6,152,141 A * | 11/2000 | Stevens et al. | 128/898 |
| 6,315,751 B1 * | 11/2001 | Cosgrove et al. | 604/5.01 |

OTHER PUBLICATIONS

Gottlob et al., "Anastomoses of Small Arteries and Veins by Means of Bushings and Adhesive," J Card Surg. 1968;9:337–341.

Guyton et al., "A Mechanical Device for Sutureless Aorta–Sapheneous Vein Anastomosis," Ann Thorac Surg. 1979;28:342–345.

Holt et al., "A New Technique for End–to–End Anastomosis of Small Arteries," Surgical Forum, v. 11,1960, pp. 242–243.

Inokuchi, "A new type of vessel–suturing apparatus," (1958) AMA Arch. Surg. 77:954–957.

Inokuchi, "Stapling device for end–to–side anastomosis of blood vessels" (1961) arch. Surg. 82:37–31.

Lanzetta et al., "Long–term Results of 1 Millimeter Arterial Anastomosis Using the 3M Precise Microvascular Anastomotic System," Microsurgery; 1992; 13:313–320.

Li et al., "End–to–side–anastomosis in the Dog using the 3M Precise Microvascular Anastomotic System: A Comparative Study," J Reconstruct Microsurg, 1991;7(4):345–350.

Miller, "The Russian Stapling Device," New York Sci., 196325:378–381.

Nakayama et al., "A Simple New Apparatus for Small Vessel Anastomosis (free autograft of the sigmoid included)," Surgery, 1962;52(6):918–931.

Narter et al., "An Experimental Method for Nonsuture Anastomosis of the Aorta," surg Gyne & Obs, 1964;632–361.

Olearchyk, "Vasilli I Kolesov—a Pioneer of Coronary Revascularization by Internal Mammary–coronary Artery Grafting," J Thorac. Surg. 1988;98(1)13–18.

Ragnarsson et al., "Microvenous End–to–side Anastomosis; An experimental study comparing the UNILINK System and Sutures," J. Reconstruct Microsurg. 1989; 5(3): 217–224.

Ragnarsson et al., "Arterial End–to–side Anastomosis with the UNILINK System," Ann Plastic Surg, 1989;22(3): 405–415.

Rohman et al., "Double coronary artery–internal mammary artery anastomoses, tantalum ring technique," (1960) Surg. Forum 11:236–243.

Vogelfanger et al. "A concept of automation in vascular surgery: a preliminary report on a mechanical instrument for arterial anastomosis," (1958) Can. J. Surg. 58:262–265.

Baumgartner et al., "Reappraisal of Cardiopulmonary Bypass with Deep Hypothermia and Circulatory Arrest for Complex Neurosurgical Operations," Surgery, 1983;94(2):242–249.

Berger and Barsamian, "Iliac or Femoral Vein–to–Artery Total Cardiopulmonary Bypass,"*Ann Thorac Surg*, 1966:2(3):281–289.

Fiore et al., "High–risk Aortic Aneurysm Repair with Partial Cardiopulmonary Bypass," *Journal of Vascular Surgery*, 1987;6(6):563–666.

Golding, "New Cannulation Technique for the Severely Calcified Ascending Aorta," *J. Thorac Card Surg*, 1985;90(4):826–627.

Hines and Rivera, "Femoral–femoral Bypass, Non–invasive hemodynamic evaluation," J Card Surg. 1984;25:230–232.

Jensen et al., "Femoral–femoral Cardiopulmonary Bypass Prior to induction of Anaesthesia in the Management of Upper Airway Obstruction," *Can Anaesth Soc J*, 1983;30(3):270–272.

Mattox and Beall, Jr., "Resuscitation of the Moribund Patient Using Portable Cardiopulmonary Bypass", *Ann Thorac Surg*, 22(5):436–442/

Okamoto et al., "Studies of Controlled Repertusion After Ischemic VIII. Regional blood cardioplegic reperfusion during total vented bypass without thoracotomy: A new concept,"*J Thorac Card Surg*. 1986;92:553–563.

Phillips et al., "Percutaneous initiation of Cardiopulmonary Bypass," *Ann Thorac Surg*. 1983;36(2):46–80.

Pillai et al., "Elective Femoro–femoral Bypass for Operations on the Heart and Great Vessels," *J Thorac Card Surg*, 1984;88(4):635–637.

Winton and Salerno, "Femorofemoral Bypass for Temporary Cardiac Support in Heart Surgery," *The Canadian Journal of Surgery*,1983;26(5):465–468.

Berger, et al., "Clinical Applications of Femoral Vein–to–Artery Cannulation for Mechanical Cardiopulmonary Support and Bypass," *The Annals of Thoracic Surgery*, vol. 12, No. 2, Feb. 1975; pp. 163–169.

Zapol, et al., "Venovenous Bypass With a Membrane Lung to Support Bilateral Lung Lavage," *JAMA*, vol. 251, No. 24, Jun. 22/29, 1984, pp. 3269–3271.

May, et al., "Emergency Bypass for the Community," *The American Journal of Surgery*, vol. 122, Aug. 1971, pp. 258–259.

Lefemine, et al., "Extracorporeal Support of the Circulation by Means of Venoarterial Bypass With an Oxygenator," *The Journal of Thoracic and Cardiovascular Surgery*, vol. 62, No. 4, Nov. 1971, pp. 769–780.

Mattox, et al., "Application of Portable Cardiopulmonary Bypass to Emergency Instrumentation," *Medical Instrumentation*, vol. 11, No. 6, Nov.–Dec. 1977, pp. 347–349.

Aufiero and Pae, "Extracorporeal Cardiopulmonary Support for Resuscitation and Invasive Cardiology Outside the Operating Suite," Section V, Clinical Application and Management of CPB, no date, pp. 682–692.

Fried et al., "Single Pump Mechanically Aspirated Venous Drainage (SPMAVD) for Cardiac Reoperation," *Perfusion*, 1995;10:327–332.

Fried et al., "Single Pump Mechanically Aspirated Venous Drainage (SPMAVD) for Cardia Reoperation," *Perfusion*, 1996; 11:351–353.

Kugai et al., "An Vitro Evaluation of Venous Cannula in a Simulated Partial (Femoral–femoral) Cardiopulmonary Bypass Circuit," *Artificial Organs*, 1995;19(2):154–160.

McCusker et al., "High–flow Femora–femoral Bypass Utilizing Small Cannulae and a Centrifugal Pump on the Venous Side," *Perfusion*, 1992;7:295–300.

Phillips et al., "Percutaneous Cardiopulmonary Bypass: Application and Indication for Use," *Ann Thorac Surg*. 1989;47:121–123.

Phillips et al., "Percutaneous Initiation of Cardiopulmonary Bypass," *Ann Thorac Surg*, 1983;36(2):223–225.

Solomon et al., "Augmented Femoral Venous Return," *Ann Thorac Surg*. 1993;55:1262–1263.

Broderick et al., "Peripheral Cardiopulmonary Support During High–risk Angioplasty," Indiana Medicine, Oct. 1990, pp. 716–721.

Jones, et al., "Safe Use of Heparin–coated Bypass Circuits Incorporating a Pump–Oxygenator," Ann Thorac Surg, 1994; 57:815–819.

Read et al., "Improved Cannulation Method for Extracorporeal Membrane Oxygenation," *Ann Thorac Surg*. 1990;50:670–671.

Richenbacher and Marks, "Cannula Selection and Cannulation Techniques for nonpulsatile Mechanical Ventricular Assistance," *Artif. Organs*, 1995;19(6):519–524.

Satoh et al., "Clinical Application of Percutaneous Left Ventricular Support with a Centrifugal Pump," *ASAIO Journal*, 1993, pp. 153–155.

Shawl et al., "Percutaneous Cardiopulmonary Bypass Support in the Catheterization Laboratory: Technique and Complications," *American Heart Journal*, 1990;120)1:195–203.

Sivananthan et al., "Coronary Angioplasty in High Risk Patients with Percutaneous Cardiopulmonary Support," *European Heart Journal*, 1994;12:1057–1062.

Taub et al., "Extracorporeal Membrane Oxgenation for Percutaneous Coronary Angioplasty in High Risk Patients," *Trans Am Soc Artif Intern Organs*, 1989;35:664–666.

* cited by examiner

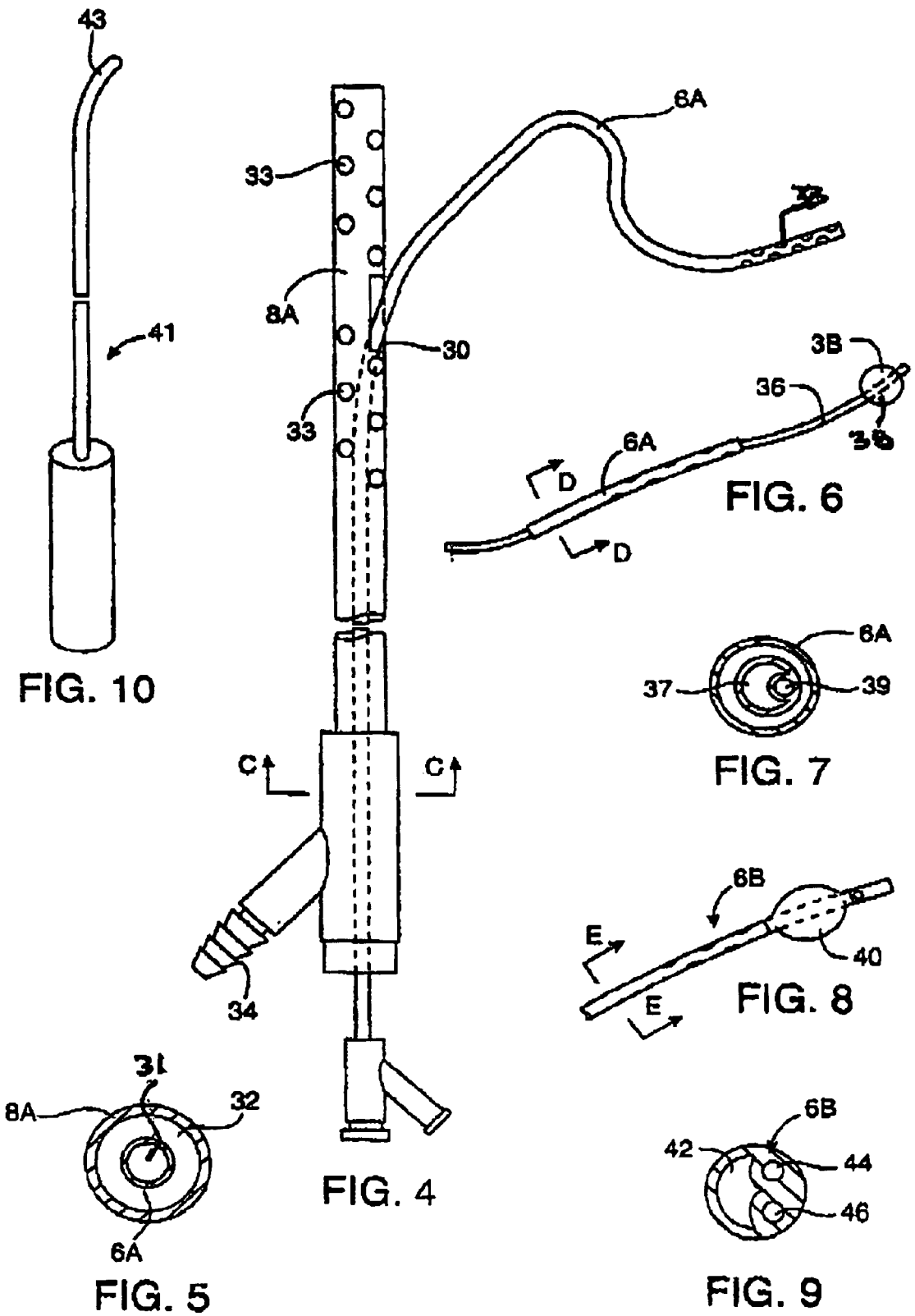

METHODS AND DEVICES FOR MAINTAINING CARDIOPULMONARY BYPASS AND ARRESTING A PATIENT'S HEART

CROSS REFERENCE TO RELATED APPLICATION

This application is a division of U.S. patent application Ser. No. 09/401,734, filed on Sep. 23, 1999, now U.S. Pat. No. 6,443,922 which is a division of application Ser. No. 08/789,223, filed Jan. 24, 1997, now U.S. Pat. No. 5,957,879 the complete disclosure of all of which is hereby incorporated herein by reference for all purposes.

BACKGROUND OF THE INVENTION

The present invention relates to systems for arresting a patient's heart and maintaining a patient on cardiopulmonary bypass. Such systems are used when performing surgical procedures, such as coronary artery bypass grafting, on an arrested heart.

In conventional open-heart surgery, the patient's breast bone is sawed open, the chest is spread apart, and the heart is accessed through the large opening created in the patient's chest. The patient is placed on cardiopulmonary bypass and the patient's heart is then arrested using catheters and cannulae which are inserted directly into the large arteries and veins attached to the heart through the large opening in the chest. The arterial cannula typically passes through the wall of the ascending aorta and a cross-clamp is applied to the ascending aorta to isolate the coronary arteries from the remainder of the arterial system. A venous cannula passes through the right atrium for withdrawing blood from the patient.

Recent developments in cardiac surgery have enabled surgeons to perform coronary artery bypass grafting and valve repair and replacement procedures without creating a large opening in the patient's chest. These developments have significantly reduced trauma to the patient by eliminating the need for sawing open the breast bone and opening the patient's chest. Such procedures are disclosed in U.S. Pat. Nos. 5,452,733 and 5,571,215 which are hereby incorporated by reference.

In order to perform such surgical procedures, the patient's heart must be arrested and the patient placed on cardiopulmonary bypass without direct access to the heart. Catheters and cannulae for arresting the patient's heart and establishing bypass without requiring direct access to the patient's heart are disclosed in U.S. Pat. Nos. 5,584,803 and 5,558,644 which are hereby incorporated by reference.

The systems described in U.S. Pat. Nos. 5,584,803 and 5,558,644 include an aortic occlusion device which has a balloon to occlude the ascending aorta and a lumen to deliver cardioplegic fluid for arresting the patient's heart. The aortic occlusion device replaces the conventional external cross-clamp and advantageously reduces the amount of displacement and distortion of the aorta. Minimizing distortion of the aorta may reduce the amount of emboli released and, therefore, may reduce stroke incidents.

A venous cannula withdraws blood from the patient and blood is returned to the patient through an arterial cannula which is placed at a peripheral artery such as the femoral artery. In a preferred embodiment, the aortic occlusion device passes through the arterial cannula thereby minimizing the number of penetrations in the patients vascular system.

The systems described in U.S. Pat. Nos. 5,584,803 and 5,558,644 also include an endovascular coronary sinus catheter for retrograde perfusion of a cardioplegic agent, preferably blood cardioplegia, via the coronary sinus. The coronary sinus catheter preferably passes through the internal jugular vein and has an inflatable balloon for occluding the coronary sinus. An endovascular venting catheter extends through the tricuspid and pulmonary valves for venting the pulmonary artery.

Although the endovascular bypass system has performed admirably and has enabled surgeons to perform less invasive cardiac procedures, the extracorporeal bypass circuit which couples the catheters and cannulae to the cardiopulmonary bypass elements may be optimized.

Thus, a specific object of the present invention is to provide an extracorporeal flow circuit for use with endovascular cardiopulmonary bypass systems.

SUMMARY OF THE INVENTION

In accordance with the present invention, methods and devices for maintaining cardiopulmonary bypass support and arresting the patient's heart are provided.

In a first aspect of the invention, a method of withdrawing blood from a patient and arresting the patient's heart is provided. An aortic occlusion device has an occluding member, a lumen and first and second branches coupled to the lumen. The first branch is coupled to a source of cardioplegic fluid, preferably blood cardioplegia, and the second branch is coupled to a pump, preferably a non-occlusive pump such as a centrifugal pump. A venous cannula is also coupled to the pump for withdrawing blood from the patient. The aortic occlusion device is then inserted into the patient so that the occluding member is positioned in the ascending aorta. The occluding member is then expanded to occlude the ascending aorta and cardioplegic fluid is delivered through the lumen in the aortic occlusion device to arrest the patient's heart. An advantage of the present invention is that a single pump is used for withdrawing blood through the venous cannula and the aortic occlusion device. The single pump reduces the complexity of multi-pump systems.

In another aspect of the present invention, another method of withdrawing blood from the patient is provided. A venting catheter is passed through the patient's tricuspid and pulmonary valves and a venous cannula is positioned in an artery of the patient. The venting catheter and venous cannula are both coupled to a pump, preferably a non-occlusive pump such as a centrifugal pump. An advantage of coupling the venous cannula and venting catheter to the same pump is that the system becomes self-regulating in that blood is withdrawn through the venous cannula when low flows are achieved through the vent catheter.

In yet another aspect of the invention, a method of withdrawing and returning blood to a patient supported by a bypass system is provided. A venous cannula is inserted into the venous system for withdrawing blood from the patient and an arterial cannula is inserted into the arterial system for returning blood to the patient. A venous line is coupled to the venous cannula and blood is withdrawn from the patient through the venous cannula and venous line. The venous cannula directs the blood to at least one pump which then pumps the blood through an arterial line to the arterial cannula. A blood storage element is coupled to the arterial line and is used to change the amount of blood in the perfusion circuit as needed. In a preferred aspect of the method, an outlet of the blood storage element is coupled to the venous line so that the blood storage element is in parallel with the pump. In another preferred aspect of the invention, the first and second lumens are slidably coupled together. The blood storage element advantageously permits the perfusionist to actively adjust the amount of blood in the perfusion circuit by withdrawing or adding blood to the blood storage element using the pump.

These and other aspects of the invention will become apparent from the following description of the preferred embodiments.

BRIEF DESCRIPTION OF THE DRAWINGS

FIG. 4 shows a venous cannula and a venting catheter extending therethrough.

FIG. 5 is a cross-sectional view of the venous cannula and venting catheter of FIG. 4 about line C—C.

FIG. 6 shows a flow directing catheter used to direct the venting catheter.

FIG. 7 is a cross-sectional view of the flow directing catheter and venting catheter of FIG. 6 about line D—D.

FIG. 8 shows the distal tip of another preferred venting catheter.

FIG. 9 is a cross-sectional view of the venting catheter of FIG. 8 about line E—E.

FIG. 10 shows an obturator for use with the venting catheters of FIGS. 4–9.

DESCRIPTION OF THE PREFERRED EMBODIMENTS

Figure 1:
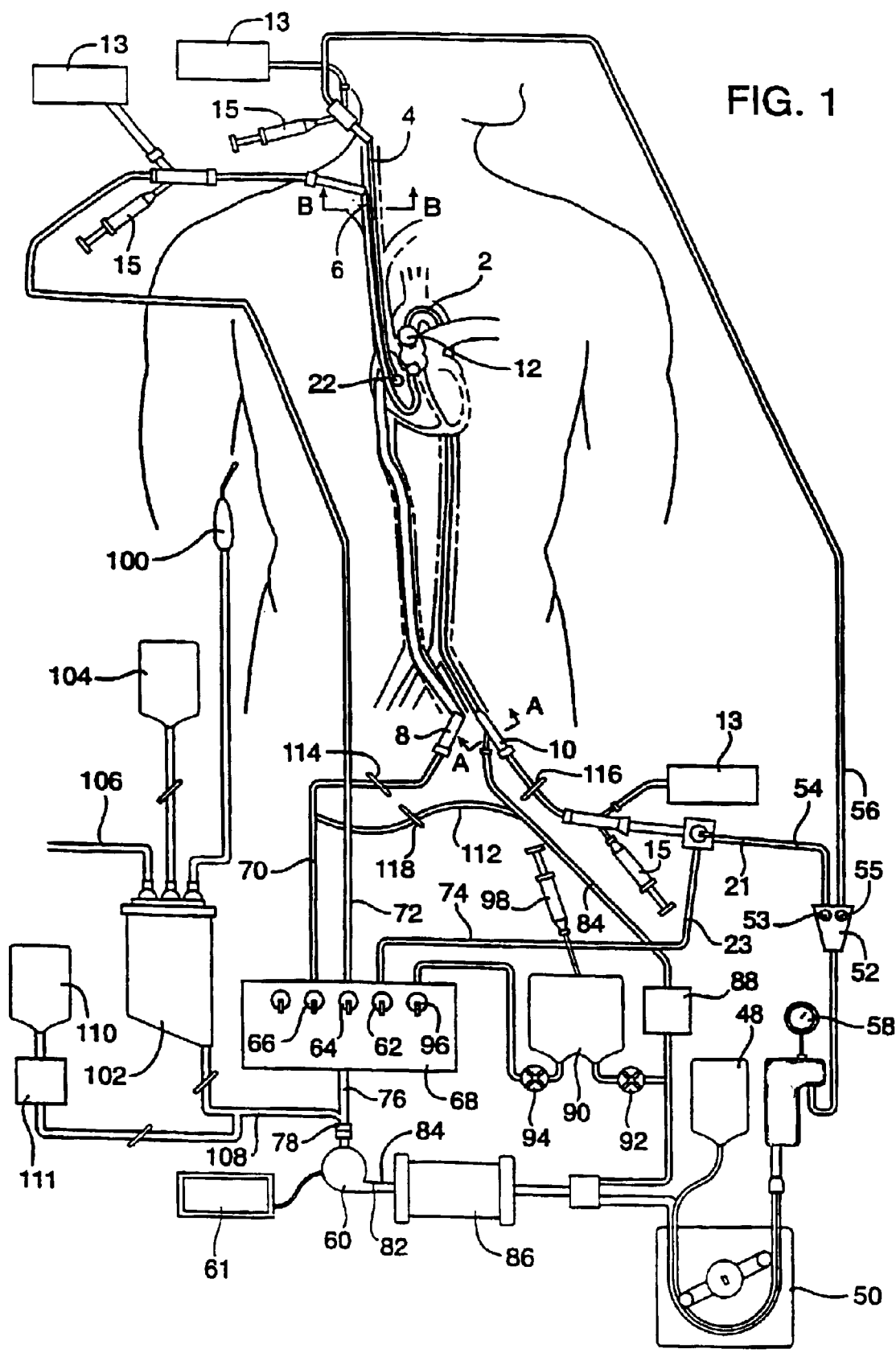
FIG. 1 shows a system for arresting a patient's heart and maintaining bypass support according to the present invention.

Referring to FIG. 1, a cardiopulmonary bypass system according to the present invention is shown. The cardiopulmonary bypass system includes an aortic occlusion device 2, an endovascular coronary sinus catheter 4, and an endovascular venting catheter 6. Blood is withdrawn from the patient through a venous cannula 8 and returned to the patient through an arterial cannula 10. The description of the invention begins with a discussion of the various catheters 2, 4, 6 and cannulae 8, 10 of a preferred endovascular catheter and cannula system. Although the following describes a preferred endovascular system, other systems may be used without departing from the scope of the invention.

The aortic occlusion device 2 preferably passes through the femoral artery or subclavian artery and into the ascending aorta. The catheter 2 has an occluding member 12, which is preferably a balloon, for occluding the ascending aorta.

Figure 2:
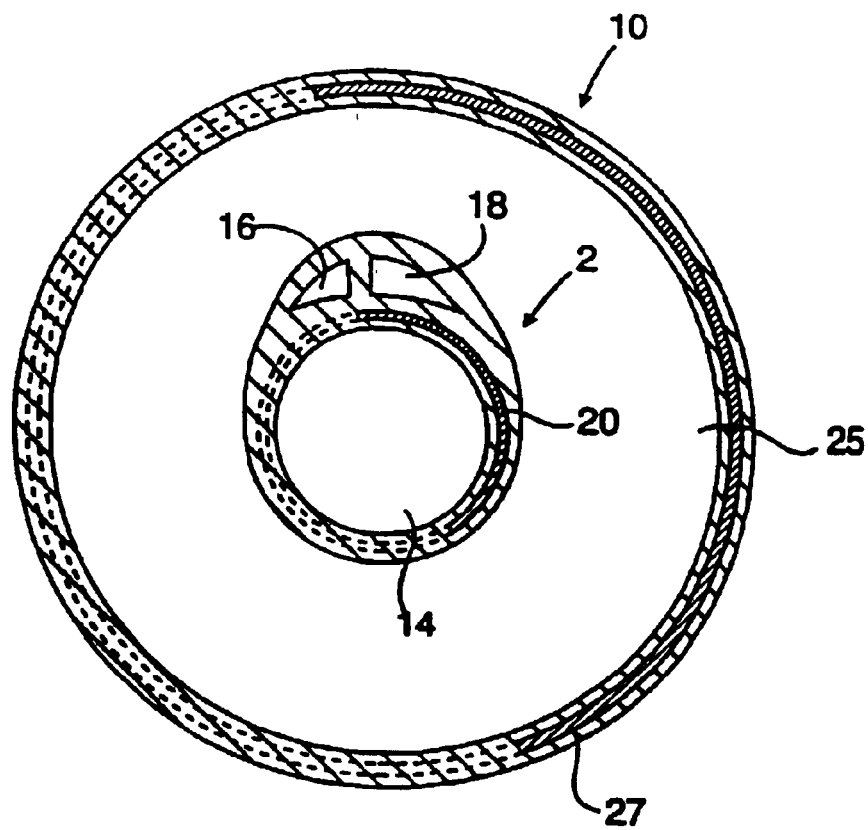
FIG. 2 is a cross-sectional view of an aortic occlusion device and an arterial cannula around line A—A of FIG. 1.

Referring to the cross-sectional view of FIG. 2, the aortic occlusion device 2 has a first lumen 14 having an outlet distal to the occluding member 12 for delivering cardioplegic fluid to arrest the patient's heart. A second lumen 16 is coupled to a pressure monitor 13 to monitor pressure distal to the occluding member 12 and a third lumen 18 is coupled to a syringe 15 for delivering inflation fluid to the occluding member 12. A member 20, which is wound in a helical manner, reinforces the catheter 2. The second lumen 16 may be eliminated by monitoring pressure through the first lumen 14 or by providing a pressure transducer. The first lumen 14 of the aortic occlusion device 2 is fluidly coupled to a first branch 21 (see FIG. 1), which is used for perfusing cardioplegic fluid, and a second branch 23 (see FIG. 1), which is used for venting blood from the heart as will be described below. Aortic occlusion devices are described in U.S. Pat. Nos. 5,584,803, 5,478,309, and 5,433,700 and U.S. patent application Ser. No. 08/782,113, now U.S. Pat. No. 682,171, entitled "Multi-Lumen Catheter and Method of Manufacture," filed Jan. 13, 1997, by inventors Timothy Corvi and John Stevens, which are all hereby incorporated by reference.

Still referring to FIG. 2, the aortic occlusion device 2 preferably passes through a lumen 25 in the arterial cannula 10 in the manner described in U.S. Pat. Nos. 5,584,803 and 5,478,309 which are hereby incorporated by reference. The arterial cannula 10 also has a reinforcing member 27 wound in a helical manner and a preferred arterial cannula 10 is described in U.S. patent application Ser. No. 08/749,683, entitled "Cannula and Method of Manufacture and Use," filed Nov. 15, 1996, now U.S. Pat. No. 5,863,366, by inventor David Snow, which is also hereby incorporated by reference. The aortic occlusion device 2 and the arterial cannula 10 may also be coupled together into a single, multi-channel catheter as described in U.S. Pat. No. 5,312,344, however, it is preferred to separate the aortic occlusion device 2 from the arterial cannula 10 for a number of reasons such as being able to replace the aortic occlusion device 2 without taking the patient off cardiopulmonary bypass. The aortic occlusion device 2 may also pass through a puncture in the ascending or descending aorta similar to the blood vessel occlusion trocar disclosed in U.S. Pat. No. 5,499,996.

Figure 3:
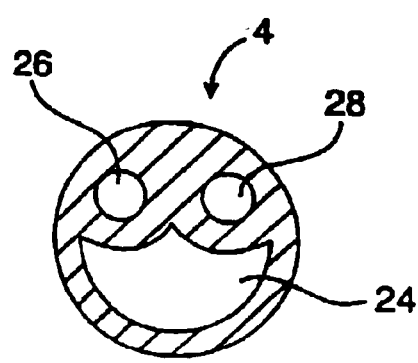
FIG. 3 is a cross-sectional view of a coronary sinus catheter about line B—B of FIG. 1.

The coronary sinus catheter 4 is used for retrograde delivery of cardioplegic fluid via the coronary sinus. Thus, both antegrade and retrograde delivery of cardioplegic fluid are provided with the aortic occlusion device 2 providing antegrade perfusion and the coronary sinus catheter 4 providing retrograde perfusion. The coronary sinus catheter 4 preferably passes through the internal jugular vein, through the right atrium and into the coronary sinus. An occluding member 22, which is preferably a balloon, is used to occlude the coronary sinus. Referring to the cross-sectional view of FIG. 3, a first lumen 24 is used for infusing cardioplegic fluid, preferably blood cardioplege, a second lumen 26 is coupled to a pressure monitor 13 and a third lumen 28 is coupled to a syringe 15 for inflating the occluding member 22. The first and second lumens 24, 26 have outlets distal to the occluding member 22 for infusing cardioplege distal to the occluding member 22 and for measuring pressure distal to the occluding member 22. Endovascular coronary sinus catheters are disclosed in U.S. Pat. No. 5,558,644 which is hereby incorporated by reference.

The venting catheter 6 preferably extends through the internal jugular vein, through the right atrium, and through the tricuspid and pulmonary valves so that a distal tip 28 is in the pulmonary artery. The venting catheter 6 is used to decompress the heart through the pulmonary vasculature and to aid the venous cannula 8 in withdrawing blood from the patient. An advantage of the venting catheter 6 is that it partially opens the pulmonary and tricuspid valves to enhance blood removal through the venous cannula 8. The venting catheter 6 can also be used as a diagnostic tool in that high flows through the venting catheter 6 may indicate a problem with the venous cannula 8 such as improper placement. A further description of the venting catheter 6 is provided below in connection with the description of FIGS.

8 and 9. Although it is preferred to provide a venting catheter 6, venting of the pulmonary artery may also be accomplished using trocar, needle or the like which penetrates the wall of the pulmonary artery. Aortic occlusion devices, coronary sinus catheters, venting catheters, and arterial and venous cannulae may be purchased from Heartport, Inc. of Redwood City, Calif.

Referring to FIGS. 4 and 5, another venting catheter 6A and venous cannula 8A are shown. The venting catheter 6A extends through the venous cannula 8A thereby eliminating the need for an independent access site for the venting catheter 6A. The venous cannula 8A has a lumen 32 which receives the venting catheter 6A and a hemostasis valve (not shown) which seals the area between the venting catheter 6A and venous cannula 8A. The venous cannula 8A also preferably has an opening 30 through which the venting catheter 6A extends. Venous blood is withdrawn through openings 33 and pass through a line (not shown) connected to a barbed connector 34. The venting catheter 6A has a lumen 31 and openings 33 at a distal end for withdrawing blood from the pulmonary artery. Referring to FIGS. 6 and 7, a flow-directing catheter 36 having a flow-directing element 38, such as a balloon, may be used to help position the venting catheter 6A. The flow-directing catheter 36 has a first lumen 37 and a second lumen 39 with one of the lumens being used to inflate the flow-directing element 38 and the other lumen either receiving a guidewire or being used for pressure measurement. Referring to FIG. 10, a specialized obturator 41 having an angled tip 43 is used to direct the venting catheter 6, 6A through the opening 30 in the venous cannula 8A.

Referring to FIGS. 1, 8 and 9, the venting catheter 6 has a flow-directing element 40, such as a balloon, for directing the venting catheter 6B through the tricuspid and pulmonary valves. The venting catheter 6 has a first lumen 42 for venting blood from the pulmonary artery, a second lumen 44 for monitoring pressure with the pressure monitor 13 or receiving a guidewire, and a third lumen 46 coupled to syringe 15 for inflating the flow-directing element 40. The catheter may also have a shaped distal portion which is configured to direct the distal tip through the tricuspid and pulmonary valves.

Referring again to FIG. 1, the aortic occlusion device 2 and coronary sinus catheter 4 are both coupled to a source of cardioplegic fluid 48. A preferred cardioplegic fluid is blood cardioplegia which contains a mixture of cardioplegic agent and blood. Blood is withdrawn from the extracorporeal bypass circuit, which will be described in greater detail below, combined with the cardioplegic agent, and delivered to the catheters with a roller pump 50. A manifold 52 having valve operators 53, 55 regulates the flow rate of cardioplegic fluid through cardioplege feed lines 54, 56 leading to the catheters 2, 4.

The pressure of the cardioplegic fluid being delivered to the patient's vascular system is measured to prevent overpressure. Pressure monitoring is particularly important when infusing the cardioplegic solution since overpressure can damage the blood and coronary vessels and can increase oxygen demand by distending the heart. As mentioned above, the aortic occlusion device 2, coronary sinus catheter 4 and venting catheter 6 all include lumens for pressure monitoring. A pressure monitor 58 also measures the delivery pressure of the cardioplege solution. The system may also include pressure alarms (not shown) which provide visual or audible signals when high or low pressure limits are reached.

The endovascular cardiopulmonary bypass system described above withdraws blood from the patient through the venous cannula 8, venting catheter 6 and aortic occlusion device 2. The venous cannula 8 and venting catheter 6 are generally withdrawing blood throughout the bypass procedure while venting through the aortic occlusion device 2 is intermittent. In many conventional perfusion circuits, a number of pumps, typically roller pumps, would be used to accomplish these tasks. In accordance with the present invention, a single pump 60, preferably a centrifugal pump, is used to perform at least two, and preferably all three, of these tasks. It is preferred to use a centrifugal pump rather than a roller pump since roller pumps are positive displacement pumps which can create dangerously high negative and positive pressures. If a roller pump is used, it is preferred to provide a pressure relief valve or a pressure alarm to prevent overpressure. Another advantage of using the single pump 60 is ease of operation since the user must concentrate on only one pump rather than three or more. A pump controller 61 is used to control the pump. Preferred pumps include the Delphin by Sarns, the Lifestream by Bard, and the Biomedicus by Medtronic.

The amount of blood being withdrawn through the catheters 2, 6 and cannula 8 is regulated by valves 62, 64, 66 on a manifold 68. The manifold 68 receives blood through a venous line 70 from the venous cannula 8, a line 72 from the venting catheter 6, and a vent line 74 from the aortic occlusion device 2. The vent line 74 extends from the second branch 23 of the aortic occlusion device 2 which is fluidly coupled to the first lumen 14. The valves 62, 64, 66 regulate flows through the aortic occlusion device 2, venous cannula 8 and venting catheter 6, respectively. The manifold 68 is preferably provided together with the various lines and catheters already connected together in a sterilized package. The lines 70, 72, 74 all merge into a common line 76 which has a connector 78 for connecting to a pump inlet 80. Thus, an advantage of the present system is that only one connection is required to couple the catheters and cannula to the pump inlet 80 after the catheters and cannulae are removed from the sterilized packaging. The present invention provides clear advantages over conventional perfusion circuits by eliminating the number of connections between catheters, cannulae and the various pumps thereby reducing the set-up time.

After passing through the pump 60, blood passes through a pump outlet 82 and into an arterial line 84. The arterial line 84 passes through an oxygentor/heat exchanger 86, which is preferably a membrane-type oxygenator/heat exchanger, and through a filter/bubble trap 88 and is returned to the patient through the arterial cannula 10. Preferred oxygenator/heat exchangers 86 include the Affinity by Avecor and the Maxima by Medtronic. The filter/bubble trap 88 may be dispensed with if the oxygenator/heat exchanger 86 is capable of performing the functions of the filter/bubble trap 88. If a separate filter/bubble trap 88 is used preferred filter/bubble traps include the H-690 by Bard and the AF1040D by Baxter.

Another advantage of the present system is that the system is closed and does not have an air/blood contact surface which generally occurs when using open cardiotomy reservoirs. Reducing or eliminating air/blood contact advantageously reduces complement activation and other humoral mediated response mechanisms. Another benefit of the present invention is a reduced priming volume as compared to conventional systems having open cardiotomy reservoirs. A reduced priming volume will reduce hemodilution and will result in higher hematocrits and, thus, more oxygen carrying capacity and buffering capability. A reduction in blood clotting factor dilution may also reduce bleeding complications.

Fluctuations in the volume of blood handled by the perfusion system are accommodated with a blood storage element 90. When a patient is on cardiopulmonary bypass, the volume of blood in the extracorporeal circuit may increase or decrease throughout the procedure. For example, blood in the circuit may be lost to field suction or blood may be added to the circuit when it is desired to reduce the blood volume in the patient. The blood storage element 90 provides the perfusionist with the flexibility to change the blood volume in the perfusion circuit for these and other purposes. The blood storage element 90 may be any type of storage element 90 and is preferably a collapsible bag such as the BMR 1900 by Baxter.

The blood storage element 90 is preferably configured in parallel with the pump 60, however, it may also be configured in series with the pump 60. Valves 92, 94 and valve 96, which is preferably mounted to the manifold 68, regulate flow through the blood storage element 90. Although valves 92, 94, 96 are preferred, clamps may also be used instead of valves, however, valves 92, 94, 96 are preferred so that the flow rate into and out of the blood storage element 90 may be regulated. The valves 92, 94, 96 are particularly useful for providing a low, continuous flow through the blood storage element to minimize clotting of stagnant blood. A syringe 98 filled with heparin may also provided to reduce clotting in the blood storage element 90. Furthermore, the entire perfusion circuit and all of the catheters and cannulae disclosed herein may be coated with a biocompatible coating, such as Duraflo II by Baxter or Cameda by Medtronic, to reduce clotting and damage to the blood.

A field suction device 100, for clearing the surgical field of blood, is coupled to a conventional cardiotomy reservoir 102. An IV bag 104 is also coupled to the cardiotomy reservoir 102 and a regulated wall vacuum 106 is used to draw fluid into the cardiotomy reservoir 102. A make-up line 108 leads from the cardiotomy reservoir 102 to the common line 76 and is used to draw blood into the perfusion system if required. Another source of blood 110 and a filter 111 are coupled to the common line 76 to add blood to the perfusion circuit, if required, or to prime the system.

A bridge line 112 extends between the arterial line 84 and venous line 70 for recirculating blood through the perfusion circuit and bypassing the patient. Clamps 114, 116 are closed to isolate the patient from the perfusion circuit and clamp 118 is opened to isolate the patient and recirculate blood in the perfusion circuit. The bridge line 112 is particularly useful in removing air from the perfusion circuit. If air is introduced in the circuit, clamps 114, 116 are closed, thereby isolating the patient from the circuit, and clamp 118 is opened to permit circulation of blood in the perfusion circuit. Blood is then circulated through the circuit until the air is removed through the oxygenator/heat exchanger 86 and bubble trap/filter 88. Clamp 118 may also have a partially open position so that a small flow of blood passes through the clamp 118 to reduce clotting of stagnant blood in the bridge line 112.

Figure 11:
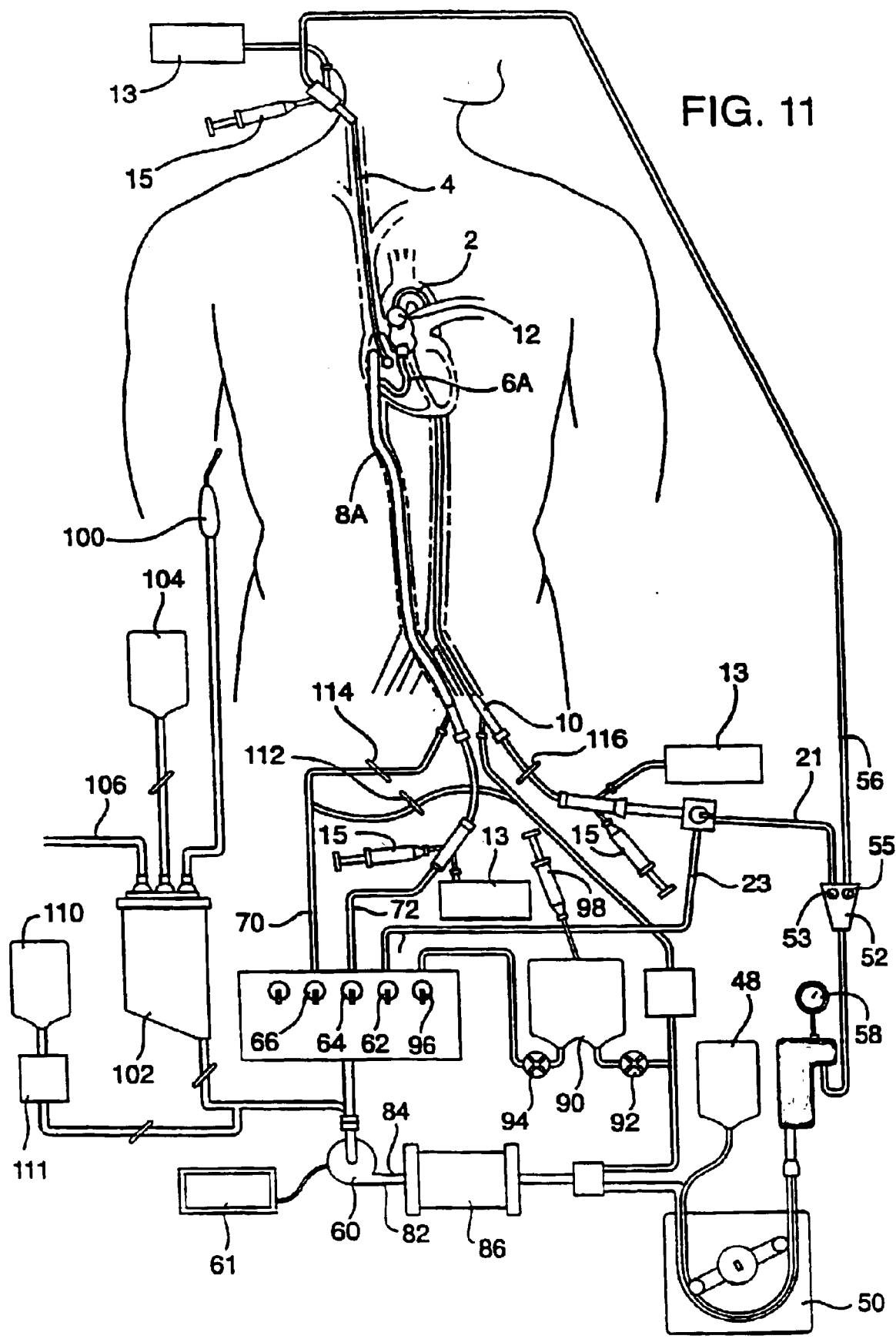
FIG. 11 shows another system for arresting a patient's heart and maintaining bypass support according to the present invention.

Referring to FIG. 11, another preferred bypass circuit is shown with like reference numerals referring to like structures. The bypass circuit has the venting catheter 6A extending through the venous cannula 8A, as described above, which advantageously reduces the number of openings in the patient's vascular system.

While the above is a preferred description of the invention, various alternatives, modifications and equivalents may be used without departing from the scope of the invention. For example, the occluding members can be an expandable member other than a balloon, the blood storage element and the bridge line may be dispensed with, and the access sites for the various catheters and cannulae may be from any other suitable vein or artery. Furthermore, the term "fluidly coupled" as used herein does not require a direct connection but, rather, a fluid communication between elements which may be through pipes, hoses, filters, valve and the like. Therefore, the above description should not be taken as limiting the scope of the invention which is defined by the claims.

What is claimed is:

1. An endovascular bypass system, comprising:
    an aortic occlusion device having a lumen and an occluding member, the occluding member being sized and configured to occlude a patient's ascending aorta;
    a venous cannula having a lumen for withdrawing blood from the patient;
    a manifold having first and second valves and first and second valve controls for controlling the first and second valves;
    a vent line extending between the lumen of the aortic occlusion device to the manifold;
    a venous line extending between the lumen of the venous cannula to the manifold; and
    the first and second valves being positioned to regulate flows through the vent line and the venous line.

2. The endovascular bypass system of claim 1, further comprising:
    an arterial cannula having a lumen for returning oxygenated blood to the patient;
    an arterial line extending from the pump outlet to the lumen of the arterial cannula; and
    a blood storage device having an inlet line and an outlet line, the inlet line being coupled to the arterial line.

3. The endovascular bypass system of claim 2, wherein:
    the outlet line of the blood storage element is coupled to the manifold; and
    the manifold having a third valve and a third valve controller for controlling the third valve, the third valve being positioned to regulate blood flow through the outlet line of the blood storage element.

4. The endovascular bypass system of claim 1, further comprising:
    a pump having am inlet and an outlet, and
    an exit line which receives blood passing through the first and second valves, the exit line being fluidly coupled to the pump inlet.

5. The endovascular bypass system of claim 1, further comprising:
    a bridge line extending between the arterial line and the venous line.

* * * * *